(12) United States Patent
Cinquin

(10) Patent No.: US 9,192,957 B2
(45) Date of Patent: Nov. 24, 2015

(54) NEBULIZER AND METHOD OF OPERATION OF A NEBULIZER

(75) Inventor: Sebastien Cinquin, La Sauvetat sur Lede (FR)

(73) Assignee: SYSTEM ASSISTANCE MEDICAL, Ledat (FR)

( * ) Notice: Subject to any disclaimer, the term of this patent is extended or adjusted under 35 U.S.C. 154(b) by 680 days.

(21) Appl. No.: 13/186,990

(22) Filed: Jul. 20, 2011

(65) Prior Publication Data

US 2012/0017894 A1 Jan. 26, 2012

(30) Foreign Application Priority Data

Jul. 20, 2010 (FR) ...................................... 10 55879

(51) Int. Cl.
| | | |
|---|---|---|
| *B05B 17/06* | (2006.01) | |
| *A61M 11/00* | (2006.01) | |
| *A61M 15/00* | (2006.01) | |
| *B05B 12/08* | (2006.01) | |

(Continued)

(52) U.S. Cl.
CPC .......... *B05B 17/0615* (2013.01); *A61M 11/005* (2013.01); *A61M 15/0085* (2013.01); *B05B 12/08* (2013.01); *B05B 12/081* (2013.01); *G01N 29/14* (2013.01); *G01N 29/4427* (2013.01); *G01N 29/4454* (2013.01); *A61M 2205/18* (2013.01); *A61M 2205/3375* (2013.01); *A61M 2205/3386* (2013.01); *A61M 2205/581* (2013.01); *A61M 2205/583* (2013.01); *B05B 12/004* (2013.01)

(58) Field of Classification Search
CPC .......... A61M 15/0085; A61M 11/005; A61M 2205/3386; A61M 2205/3389; A61M 2015/001; B05B 17/0607; B05B 12/004; B05B 17/06

USPC ............ 128/200.11–200.22, 200.24, 203.12, 128/203.15, 202.22, 205.23
See application file for complete search history.

(56) References Cited

U.S. PATENT DOCUMENTS

| | | | | |
|---|---|---|---|---|
| 4,776,990 A | | 10/1988 | Verity | |
| 5,448,222 A | * | 9/1995 | Harman | ........................ 340/566 |

(Continued)

FOREIGN PATENT DOCUMENTS

| | | |
|---|---|---|
| EP | 0 849 592 A2 | 6/1998 |
| EP | 1 026 482 A1 | 8/2000 |

(Continued)

OTHER PUBLICATIONS

French Preliminary Search Report issued Mar. 11, 2011, in French 1055879, filed Jul. 20, 2010 (with English Translation of Categories of Cited Documents).

*Primary Examiner* — Melanie Hand
*Assistant Examiner* — Aundria Hairell
(74) *Attorney, Agent, or Firm* — Oblon, McClelland, Maier & Neustadt, L.L.P.

(57) ABSTRACT

Nebulizer and method of operation of a nebulizer comprising a cupel capable of containing a liquid and a vibrating member (4) capable of emitting, under the effect of a control signal originating from a control circuit (10), an ultrasound beam making it possible to transform the liquid into mist, in which the vibrating member (4) is sensitive to the sound wave produced during the transformation of the liquid into mist and detection means (14) detect the presence and/or the absence and/or the value of a sound signal originating from the vibrating member, or of a signal corresponding to a sound signal originating from said vibrating member.

10 Claims, 3 Drawing Sheets

(51) Int. Cl.
*G01N 29/14* (2006.01)
*G01N 29/44* (2006.01)
*B05B 12/00* (2006.01)

(56) References Cited

U.S. PATENT DOCUMENTS

| | | | |
|---|---|---|---|
| 6,357,671 B1 * | 3/2002 | Cewers | 239/102.2 |
| 6,438,239 B1 | 8/2002 | Kuechen | |
| 2006/0102172 A1 * | 5/2006 | Feiner et al. | 128/200.14 |
| 2007/0240712 A1 * | 10/2007 | Fleming et al. | 128/203.15 |
| 2007/0277816 A1 * | 12/2007 | Morrison et al. | 128/200.16 |
| 2008/0040801 A1 * | 2/2008 | Buriano et al. | 726/22 |
| 2009/0200397 A1 * | 8/2009 | Sheiman | 239/102.2 |

FOREIGN PATENT DOCUMENTS

| | | | |
|---|---|---|---|
| JP | 05123400 A * | 5/1993 | A61M 15/00 |
| WO | WO 2006/125251 A1 | 11/2006 | |
| WO | WO 2010/067239 A2 | 6/2010 | |
| WO | WO 2010/067239 A3 | 6/2010 | |

* cited by examiner

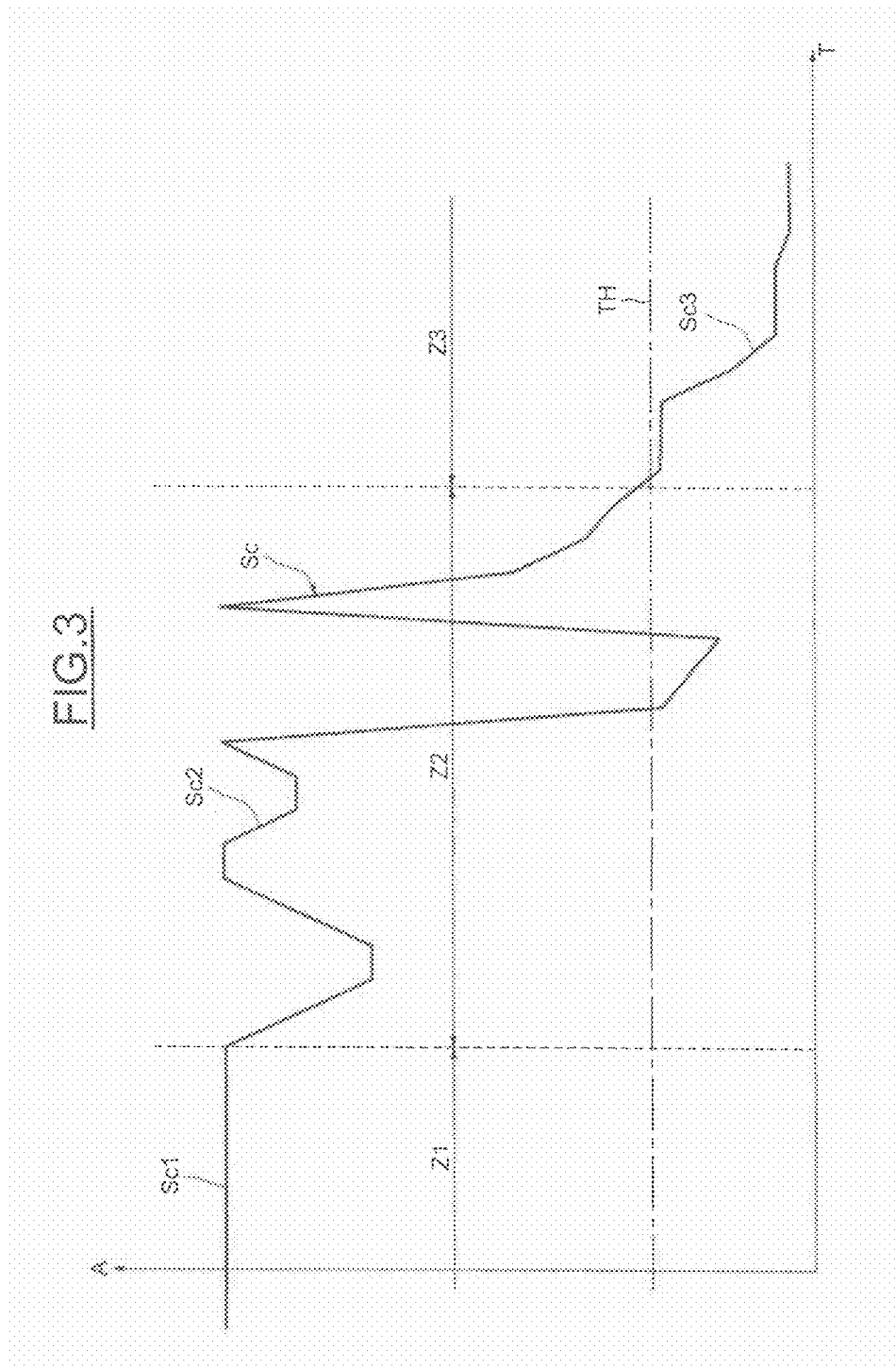

NEBULIZER AND METHOD OF OPERATION OF A NEBULIZER

The present invention relates to the field of nebulizers capable of generating a mist from a liquid, in particular a mist containing a medication, a paramedical product or a wellbeing product, in particular so that this mist is inhaled by a person.

Usually, nebulizers comprise a cupel capable of containing a liquid to be nebulized and a vibrating member, in particular a piezoelectric component, placed beneath the cupel and capable of emitting, under the effect of a control signal originating from a control circuit, an ultrasound beam making it possible to transform the liquid to be nebulized into mist. A sealing liquid, usually water, is provided in the space between the vibrating member and the cupel, in contact with the latter, this sealing liquid being used for the transfer of the ultrasound beam and forming a thermal mass making it possible to prevent a rise in the temperature of the liquid to be nebulized which could damage the medication.

When the vibrating member is operating and there is no more liquid to be nebulized in the cupel, there is a risk of damaging and of piercing the wall of the cupel and a risk of premature wear of the vibrating member.

Documents WO2006/125251 and WO2010/067239 describe nebulizers which comprise vibrating members producing ultrasound waves in order to transform the liquid into mist and which comprise additional sound sensors in order to detect the noise caused by the transformation of the liquid into mist and deliver a warning signal.

Document US 2007/240712 describes a nebulizer which comprises a vibrating member producing an ultrasound wave in order to transform the liquid into mist and in which the variation of the resonance frequency producing the ultrasound wave, or an associated electromechanical parameter, is measured in order to determine the quantity of liquid remaining. Since this variation is slight, it is therefore difficult to measure and is not reliable. This nebulizer may also comprise an additional sound sensor in order to detect the noise caused by the transformation of the liquid into mist.

The primary object of the present invention is to limit the aforementioned drawbacks and to propose a particularly simple and effective solution.

A nebulizer is proposed which comprises a cupel capable of containing a liquid and a vibrating member capable of emitting, under the effect of a control signal originating or coming from a control circuit, an ultrasound wave making it possible to transform the liquid into mist.

This nebulizer comprises detection means for detecting the presence and/or the absence of a sound signal originating from said vibrating member and/or for determining the value of such a sound signal, or of a signal corresponding to a sound signal originating from said vibrating member.

Thus, the sound wave or the noise produced during the transformation of the liquid into mist causes a vibration of the vibrating member at corresponding sound frequencies such that the detection of such sound frequencies may supply an item of information relating to the content of the cupel. In particular, if absence or nonexistence of this sound frequency or of this noise is detected, it means that there is no more liquid to be nebulized in the cupel.

According to a variant embodiment, the detection means may comprise a filter linked to the connection between the control circuit and the vibrating member and capable of delivering a filtered signal corresponding to a sound signal and an analysis means for detecting the presence and/or the absence of this filtered signal and/or the value of this filtered signal.

The absence of a signal originating from the sound sensor may be determined relative to a threshold.

A sound and/or light warning element may be subjected to the detection means in order to warn a user.

Also proposed is a method for operating a nebulizer comprising a cupel capable of containing a liquid and a vibrating member capable of emitting, under the effect of a control signal originating from a control circuit, an ultrasound wave making it possible to transform the liquid into mist.

This method may consist in choosing a vibrating member capable of detecting a sound wave, in detecting the presence and/or the absence and/or the value of a sound signal originating from said vibrating member, representative of the sound wave produced during the transformation of the liquid into mist, and in delivering a corresponding warning signal.

The detection of the presence and/or the absence of the sound signal representative of the sound wave may advantageously be achieved relative to a threshold.

According to one variant, the activation of a warning means may be caused in the event of absence of the sound signal.

According to another variant, the deactivation of the control circuit may be caused in the event of absence of the sound signal.

According to a variant embodiment, the vibrating member may be capable of emitting an ultrasound wave of which the frequency is between two and three megaHertz and the sound signal to be detected, that originates or comes from said vibrating member, may have a frequency of less than one hundred Hertz.

A nebulizer and operating modes of the latter will now be described as non-limiting examples, illustrated by the drawing in which:

FIG. 3 represents an amplitude/time graph associated with one mode of operation of the electronic circuit of FIG. 2.

Figure 1:
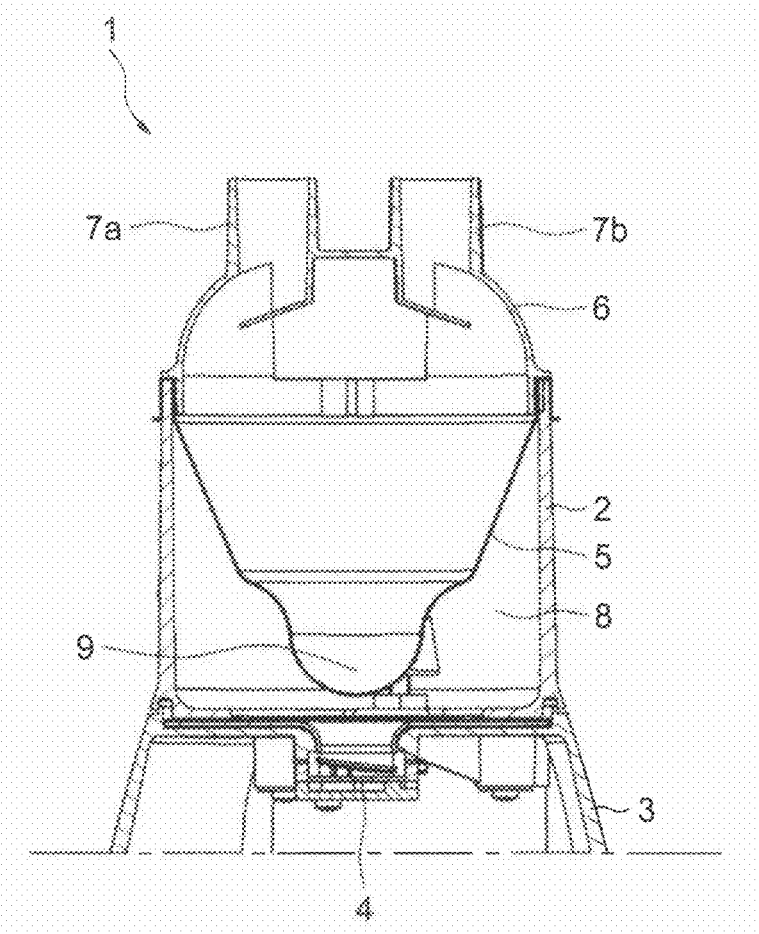
FIG. 1 represents a partial vertical section of a nebulizer.

A nebulizer 1 illustrated in FIG. 1 comprises a chamber 2 supported by a housing 3 that is partially represented, a vibrating member 4 installed in the bottom of the chamber 2, a cupel 5 with a thin wall the peripheral edge of which is supported by the edge of the chamber 2 and which is engaged in the chamber 2 so that the bottom of this cupel 5 is at a distance above the bottom of the chamber 2 and the vibrating member 4, and a lid 6 also supported by the edge of the chamber 2 and having mouths 7a and 7b.

The space 8 between the chamber 2 and the cupel 5 is, at least partially, filled with a liquid such as water, so that at least the lower portion of the cupel 5 is immersed in this liquid.

It is possible to pour into the cupel 5 a liquid 9 to be nebulized, for example a liquid containing a medication, a paramedical product or a wellbeing product.

Figure 2:
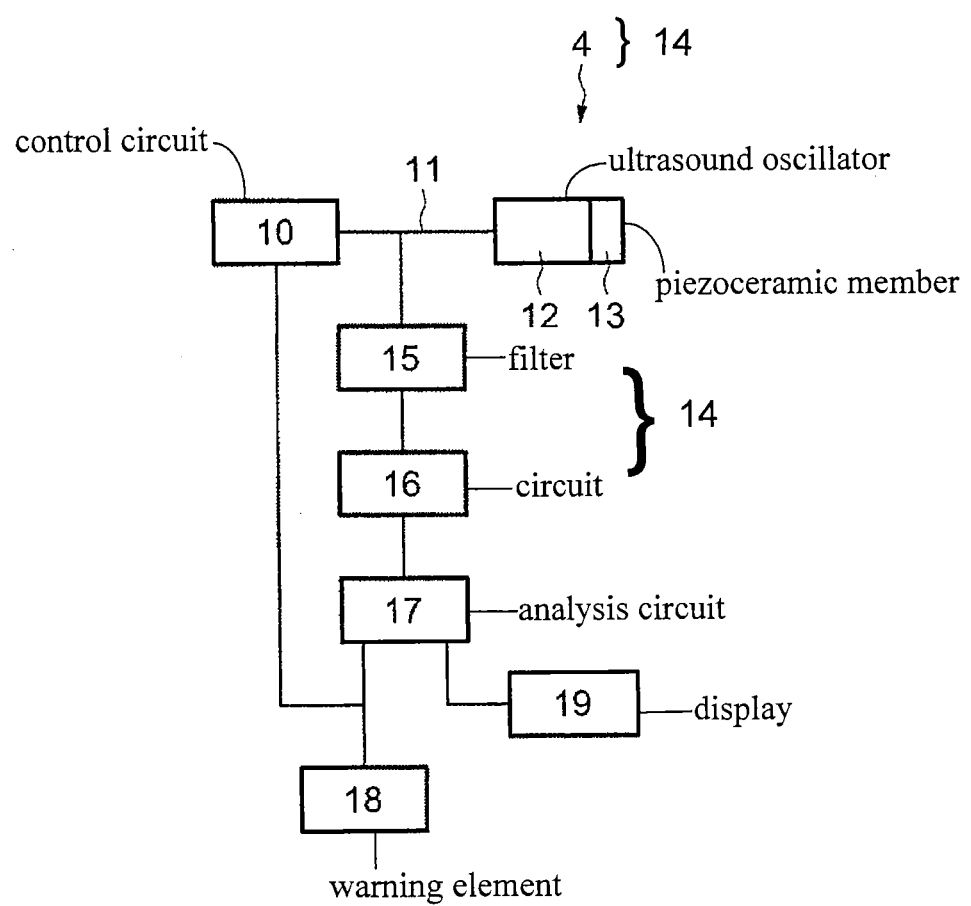
FIG. 2 represents schematically an electronic circuit associated with the nebulizer of FIG. 1.

As illustrated in FIG. 2, the vibrating member 3 is linked to an electronic control circuit 10 by a connection 11, for example a wire connection, installed in the housing 3.

Under the effect of an electric signal originating from the electronic control member 10, the vibrating member 4 emits an ultrasound beam or an ultrasound wave that is propagated in the water contained in the space 8, then through the wall of the cupel 5, then through the liquid 9 to be nebulized. Under the effect of this wave, a jet is produced locally on the surface of the liquid 9 such that a break-up of the liquid into particles makes it possible to progressively transform the liquid 9 to be nebulized into mist, the size of the particles depending on the wavelength of the wave emitted by the vibrating member 4.

The generated mist may be inhaled by a user by virtue of tubes that can be connected to the mouths 7a and 7b, for the purpose of causing air to circulate above the liquid 9 and in the lid 6 in order to carry away the mist.

According to one example, the vibrating member 4 comprises an ultrasound oscillator 12 linked to a piezoceramic member 13. The frequency of the wave emitted by the piezoceramic member 13 may be approximately 2.4 MegaHertz.

The nebulizer 1 also comprises detection means 14 for detecting the presence and/or the absence of liquid 9 to be nebulized in the cupel 5 and for notifying the user thereof. These detection means 14 are based on a detection of the presence or of the absence of the noise produced during the transformation of the liquid 9 to be nebulized into mist.

As illustrated in FIG. 2, the detection means 14 comprise a sound sensor that consists directly of the vibrating member 4. The piezoceramic member 13 of the vibrating member 4 may specifically be sensitive to the sound wave produced during the transformation of the liquid 9 to be nebulized into mist, such that the vibrating member 4 can deliver to the connection 11 a sound signal, that is to say a frequential electric signal corresponding to a sound frequency.

The detection means 14 also comprise a detection system which includes a filter 15 linked to the connection 11, making it possible to filter the sound signal, for example having a frequency of less than 100 Hertz, then a circuit 16 for amplifying and forming, by averaging or integration, the signal originating from the filter 15, making it possible to deliver a signal of voltage Sc corresponding to the sound signal.

This signal Sc is then directed towards an analysis circuit 17 capable of analysing this signal Sc according to a program and of delivering an activation signal Sa in order to activate a sound and/or light warning element 18 as a function of the value of the signal Sc and/or in order to deactivate the electronic control circuit 10. The analysis circuit 17 and the sound and/or light warning element 18 are supported by the housing 3 and are not shown in FIG. 1.

FIG. 3 illustrates one mode of analysing the value or the amplitude of the signal Sc relative to the value of a threshold TH, carried out by the analysis circuit 17.

It is assumed that a certain quantity of liquid 9 to be nebulized has been placed in the cupel 5 and the nebulizer 1 has been started in order to produce mist.

In a time zone Z1, while the cupel 5 contains sufficient liquid 9 to be nebulized, the noise produced by the nebulization is relatively loud. Consequently, the value Sc1 of the signal Sc is and remains much greater than the value of the threshold TH. The value of the threshold TH may be between 10% and 30% of the value of the signal Sc in this case.

Then, in a consecutive time zone Z2, when the liquid is running out and no more remains in the cupel 5 than a few drops of the liquid 9 to be nebulized, the noise produced by the nebulization reduces and becomes chopped. Consequently, the value Sc2 of the signal Sc falls and rises and may pass, for brief durations, below the value of the threshold TH.

Then, in a consecutive time zone Z3, when the cupel 5 becomes virtually empty or empty, the noise produced by the nebulization becomes very low and then nonexistent. Consequently, the value Sc3 of the signal Sc becomes and remains less than the value of the threshold TH.

In order to analyse the circumstances described above, the analysis circuit 17 can be programmed to compare the value of the signal Sc with the value of the threshold TH at predetermined successive comparison times according, for example, to the following arrangement.

If, at the time of a comparison, the value of the signal Sc is greater than the value of the threshold TH at a comparison time, the analysis circuit 17 will make a new comparison at the end of a predetermined long duration D1, for example equal to three minutes.

If, at the time of a comparison, the value of the signal Sc is less than or equal to the value of the threshold TH, the analysis circuit 17 will make another comparison at the end of a predetermined short duration D2, for example equal to ten seconds.

The analysis circuit 17 is programmed to be capable of counting the number of consecutive times for which the value of the signal Sc is less than or equal to the value of the threshold TH and is programmed to deliver a warning signal Ss as soon as this number reaches a predetermined value Np, for example 200 consecutive times.

Thus, the zones Z1 and Z2 are detected by the fact that the analysis circuit 17 makes comparisons spaced apart by the predetermined long duration D1 or that the predetermined value Np of the number of consecutive times for which the value of the signal Sc is less than or equal to the value of the threshold TH is not reached.

On the other hand, the zone Z3 is detected by the fact that the analysis circuit 17 has, for a number of consecutive times, made comparisons for which the value of the signal Sc is less than or equal to the value of the threshold TH, such that the predetermined value Np is reached. Then, the analysis circuit 17 generates the activation signal Sa.

In one variant, the activation signal Sa activates the sound and/or light warning element 18 so that the user places more liquid 9 to be nebulized in the cupel 5 or deactivates the electronic control circuit 10 so that the vibrating member 4 ceases to be activated.

In another variant, the analysis circuit 17 generates the activation signal Sa in order to deactivate the electronic control circuit such that the vibrating member 4 ceases to be activated automatically, it being able to be restarted only if more liquid 9 to be nebulized is placed in the cupel 5.

The above two variants may naturally be applied jointly.

The result of the foregoing is that the cupel 5 can be protected against possible damage or possible perforation if there is no liquid 9 to be nebulized in the cupel 5.

According to one variant, the analysis circuit 17 could be programmed to deliver the warning signal Sa or a separate signal, in order to control the sound and/or light warning element 18, separately, or a separate warning element, if the number of consecutive times for which the value of the signal Sc is less than or equal to the value of the threshold TH reaches a determined value that is below the value Np, in order, for example, to notify the user that only a few drops of the liquid 9 to be nebulized remain in the cupel 5.

According to another variant, also shown in FIG. 2, the value of the signal Sc, in the aforementioned zone Z1, can be representative of the quantity of liquid 9 to be nebulized that is contained in the cupel 5. In this case, the analysis circuit 17 could deliver a signal Sb relating to this quantity in order to supply an item of corresponding information to the user, for example by means of a display 19.

The present invention is not limited to the examples described above. Many other variant embodiments are possible without departing from the context defined by the appended claims.

The invention claimed is:

1. A nebulizer comprising:
    a cup to contain a liquid; and
    a vibrating member configured to emit, under an effect of a control signal originating from a control circuit, an ultrasound beam to transform the liquid into mist; and
    analysis circuitry configured to detect a sound signal originating or coming from said vibrating member, representative of a sound wave produced during the transformation of the liquid into the mist in the cup, determine variations in emitted sound associated with the liquid in the cup by comparing a value of the sound signal, which represents a quantity of the liquid in the cup, to a threshold (TH), which represents a predetermined minimum quantity of the liquid for the cup, at successive determined comparison times, count a number of consecutive different times at which the value of said sound signal, which represents the quantity of the liquid in the cup, is equal to or less than said sound signal threshold, which represents the predetermined minimum quantity of the liquid for the cup, and deliver, based on the variations in emitted sound associated with the liquid in the cup, a warning signal representing an insufficient quantity of the liquid in the cup, when the number of consecutive different times is equal to a predetermined second threshold that is different from said sound signal threshold.

2. The nebulizer according to claim 1, further comprising a sound or light warning element subjected to the analysis circuitry.

3. The nebulizer according to claim 1, wherein the vibrating member is located beneath the cup.

4. The nebulizer according to claim 1, wherein the vibrating member is a piezoceramic component.

5. A method for a nebulizer including a cup to contain a liquid and a vibrating member configured to emit, under an effect of a control signal originating from a control circuit, an ultrasound wave to transform the liquid into mist, the method comprising:

detecting a sound signal (Sc) originating from said vibrating member, representative of a sound wave produced during the transformation of the liquid into the mist in the cup;

determining variations in emitted sound associated with the liquid in the cup by comparing a value of said sound signal, which represents a quantity of the liquid in the cup, to a sound signal threshold (TH), which represents a predetermined minimum quantity of the liquid for the cup, at successive determined comparison times;

counting a number of consecutive different times at which the value of said sound signal, which represents the quantity of the liquid in the cup, is equal to or less than said sound signal threshold, which represents the predetermined minimum quantity of the liquid for the cup; and delivering, based on the variations in emitted sound associated with the liquid in the cup, a warning signal representing an insufficient quantity of the liquid in the cup, when the number of consecutive different times is equal to a predetermined second threshold that is different from said sound signal threshold.

6. The method according to claim 5, further comprising deactivating the control circuit when the warning signal is delivered.

7. The method according to claim 5, further comprising emitting, by the vibrating member, the ultrasound wave of which the frequency is between two and three megahertz, the sound signal to be detected, that originates from said vibrating member, having a frequency of less than or equal to one hundred Hertz.

8. The method according to claim 5, wherein said comparing compares a first value of said sound signal to said sound signal threshold during a first period of time, compares a second value of said sound signal to said sound signal threshold during a second period of time that is different than said first period of time, in response to said first value of said sound signal being greater than said sound signal threshold during said first period of time, and compares a third value of said sound signal to said sound signal threshold during a third period of time that is different from said first period of time and said second period of time, in response to said second value of said sound signal being equal to or less than said sound signal threshold during said second period of time.

9. The method according to claim 5, wherein said predetermined second threshold corresponds to a plural number of times.

10. A method of monitoring a liquid quantity within a nebulizer including a cup containing a liquid and a vibrating member configured to emit an ultrasound wave under an effect of a control signal originating from a control circuit, the method comprising:

detecting a first value of a sound signal, which represents a first quantity of the liquid in the cup, at a first time;

comparing the first value of the sound signal, which represents the first quantity of the liquid in the cup, to a threshold value, which represents a predetermined minimum quantity of the liquid for the cup;

determining whether the first value of the sound signal, which represents the first quantity of the liquid in the cup, is below the threshold value, which represents the predetermined minimum quantity of the liquid for the cup;

detecting a second value of the sound signal, which represents a second quantity of the liquid in the cup, at a second time, in response to the first value being below the threshold value, which represents the predetermined minimum quantity of the liquid for the cup;

determining whether the second value, which represents the second quantity of the liquid in the cup, is below the threshold value, which represents the predetermined minimum quantity of the liquid for the cup; and delivering a warning signal representing an insufficient quantity of the liquid for the cup to the control circuit, in response to the second value being below the threshold value.

* * * * *